(12) United States Patent
Silver et al.

(10) Patent No.: US 12,102,435 B2
(45) Date of Patent: Oct. 1, 2024

(54) SYSTEMS, DEVICES, AND METHODS FOR NON-INVASIVE AND NON-DESTRUCTIVE IMAGING AND MEASUREMENT OF TISSUE AND MATERIAL MECHANICAL PROPERTIES

(71) Applicant: OptoVibronex, LLC, Mount Bethel, PA (US)

(72) Inventors: Frederick Howard Silver, Allentown, PA (US); Istvan Horvath, Princeton, NJ (US); Nikita Uday Kelkar, Allentown, PA (US); Tanmay Manoj Deshmukh, Allentown, PA (US); Ruchit Girishchandra Shah, Colonia, NJ (US)

(73) Assignee: OptoVibronex, LLC, Mount Bethel, PA (US)

( * ) Notice: Subject to any disclaimer, the term of this patent is extended or adjusted under 35 U.S.C. 154(b) by 835 days.

(21) Appl. No.: 17/179,640

(22) Filed: Feb. 19, 2021

(65) Prior Publication Data

US 2021/0251543 A1    Aug. 19, 2021

Related U.S. Application Data

(60) Provisional application No. 62/978,799, filed on Feb. 19, 2020.

(51) Int. Cl.
*A61B 5/22*  (2006.01)
*A61B 5/00*  (2006.01)
(Continued)

(52) U.S. Cl.
CPC .............. *A61B 5/22* (2013.01); *A61B 5/0051* (2013.01); *A61B 5/0066* (2013.01); *A61B 5/08* (2013.01);
(Continued)

(58) Field of Classification Search
CPC ... A61B 5/0051; A61B 5/0066; A61B 5/7405; G01L 1/103
See application file for complete search history.

(56) References Cited

U.S. PATENT DOCUMENTS

| | | | |
|---|---|---|---|
| 5,606,971 A | 3/1997 | Sarvazyan | |
| 6,875,176 B2 | 4/2005 | Mourad et al. | |

(Continued)

FOREIGN PATENT DOCUMENTS

| | | |
|---|---|---|
| CA | 2428872 | 1/2013 |
| CN | 106361294 | 8/2019 |
| CN | 107028623 | 9/2020 |

OTHER PUBLICATIONS

Silver FH. A matter of gravity-mechanotransduction: how mechanical forces influence biological materials. Mater Sci Eng Int J, 2017; 1: 00012.

(Continued)

*Primary Examiner* — Eric F Winakur
*Assistant Examiner* — Abel Seifu Abegaz
(74) *Attorney, Agent, or Firm* — Unikel Law LLC

(57) ABSTRACT

A system, devices, and methods are described for imaging and measuring the mechanical properties of both surface and subcutaneous tissues found in living organisms, animals, and in natural and synthetic materials, and may include a first device configured to determine a modulus of a portion of bulk material or subcutaneous tissue (via measurement of vibrations), and/or determine resonant frequency of the vibrations, and a second device operably connected to the first device and configured to generate vibrations. The first device may be an optical coherence tomography device. The system may include a processor and data storage device with instructions which when executed by the processor, cause the processor to process of the frequency data and the displacement data to determine a resonant frequency of the (Continued)

material under investigation and calculate the mechanical modulus of elasticity of the material from a resonance frequency spectrum of the analyzed spectral image.

17 Claims, 8 Drawing Sheets

(51) Int. Cl.
 A61B 5/08 (2006.01)
 A61B 5/20 (2006.01)
(52) U.S. Cl.
 CPC ............. *A61B 5/201* (2013.01); *A61B 5/441* (2013.01); *A61B 5/4504* (2013.01); *A61B 5/4533* (2013.01); *A61B 5/4538* (2013.01); *A61B 5/7405* (2013.01)

(56) References Cited

U.S. PATENT DOCUMENTS

| | | | |
|---|---|---|---|
| 7,477,571 B2 | 1/2009 | Melese et al. | |
| 9,345,448 B2 | 5/2016 | Fatemi et al. | |
| 10,231,706 B2 | 3/2019 | Chen et al. | |
| 10,488,277 B2 | 11/2019 | Silver et al. | |
| 2008/0228073 A1 | 9/2008 | Silverman et al. | |
| 2009/0116032 A1 | 5/2009 | Zara | |
| 2013/0190613 A1* | 7/2013 | Boppart | A61N 7/00 600/427 |
| 2013/0218012 A1 | 8/2013 | Specht et al. | |
| 2014/0323862 A1 | 10/2014 | Silverman et al. | |
| 2017/0107558 A1* | 4/2017 | Chen | G01N 29/07 |
| 2017/0290503 A1 | 10/2017 | Larin et al. | |
| 2017/0319171 A1 | 11/2017 | Vappou et al. | |
| 2018/0328798 A1* | 11/2018 | Silver | G01L 1/103 |
| 2020/0315499 A1* | 10/2020 | Adamson | A61B 5/126 |

OTHER PUBLICATIONS

Silver FH, Silver LL. Gravity. Mechanotransduction and healing: how mechanical forces promote tissue repair. SM J Biomed Eng, 2017; 3(4): 1023.
Silver FH. Mechanosensing and Mechanochemical Transduction in Extracellular Matrix, Springer, N.Y., 2006.
Samani A, Bishopj, Luginbuhl C, Plewes DB. Measuring the elastic modulus of ex-vivo small tissue samples. Phys Med Biol, 2003; 48(14): 2183-2198.
Samani A, Zubovits J, Plewes D. Elastic moduli of normal and pathological human breast tissues: an inversion-technique-based investigation of 169 samples. PhysMed Biol, 2007; 52: 1565-1576.
Acerbi I, Cassereau L, Dean I, Shi Q, Au A, Park C, Chen YY, Liphardt J, Hwang ES, Weaver VM. Human breast cancer invasion and aggression correlates with ECM stiffening and immune cell infiltration. Integr Biol (Camb), 2015; 7(10): 1120-1134.
Lin HH, Lin HK, Lin IH, Chiou YW, Chen HW, Liu CY, Hans I, Harn C, Chiu WT, Wang YK, Shen MR, Tang MJ. Mechanical phenotype of cancer cells: cell softening and loss of stiffness sensing. Oncotarget, 2015; 6(25): 20946-20958.
Lekka M. Discrimination between normal and cancerous cells using AFM. Bionanoscience, 2016; 6: 65-80.
Emon B, Bauer J, Jain Y, Jung B, Saif T. Biophysics of tumor microenvironment and cancer metastasis: a mini review. Comput Struct Biotechnol J, 2018; (27)16: 279-287.
Yamada H, Evans FG. Strength of biological materials. Williams and Wilkins, Baltimore, USA, 1970, pp. 297.
Fung YC. Biomechanics: Mechanical properties of living tissue. (1st edn), Springer-Verlag New York, USA, 1973, pp. 568.
Dunn MG, Silver FH. Viscoelastic behavior of human connective tissues: relative contribution of viscous and elastic components. Conn Tis Res, 1983; 12: 59-70.
Lacroix AS, Duenwald-Kuehl SE, Lakes RS, Vanderby Jr R. Relationship between tendon stiffness and failure: a metaanalysis. Appl Physiol, 2013; 115(1): 43-51.
Sugimura K, Lenne PF, Graner F. Measuring forces and stresses in situ in living tissues. Development, 2016; 143(2): 186-196.
Low G, Kruse SA, Lomas DJ. General review of magnetic resonance elastography. World J Radiol, 2016; 8(1): 59-72.
Ruberti JW, Roy AS, Roberts CJ. Corneal biomechanics and biomaterials. Annu Rev Biomed Eng, 2014; 13: 269-295.
Campas O, Mammota T, Hasso S, Sperling RA, O'Connell D, Bischof AG, Maas R, Weitz DA, Mahadevan L, Ingber DE. Quantifying cell-generated mechanical forces within living cells. Nat Methods, 2014; 11(2): 183-189.
Kennedy BF, Kennedy KM, Sampson DD. A review of optical coherence elastography: fundamentals, techniques and prospects. IEEE Journal of Selected Topics in Quantum Electronics, 2014; 20(2): 272-288.
Kennedy BF, McLaughlin RA, Kennedy KM, Chin L, Curatolo A, Tien A, Latham B, Saunders CM, Sampson DD. Optical coherence micro-elastography: mechanical-contrast imaging of tissue microstructure. Biomed Opt Express, 2014a; 5(7): 2113-2124.
Drakonaki EE, Allen GM, Wilson DJ. Ultrasound elastography for musculoskeletal applications. Br J Radiol, 2012; 85(1019): 1435-1445.
Zaleska-Dorobisz U, Kaczorowski K, Pawlus A, Puchalskoc A, Inglot M. Ultrasound elastography—review of techniques and its clinical application. Adv Clin Exp Med, 2014; 23: 645-655.
Li C, Guan G, Huang Z, Johnstone M, Wang RK. Noncontact all-optical measurement of corneal elasticity. Opt Lett, 2012; 37(10): 1625-1627.
Song S, Le NM, Huang Z, Shen T, Wang RK. Quantitative shear-wave optical coherence elastography with a programmable phased array ultrasound as the wave source. Opt Lett, 2015; 40(21): 5007-5010.
Shah R, Pierce MC, Silver FH. A method for non-destructive mechanical testing of tissues and implants. J Biomed Mater Res A, 2016; 105(1): 15-22.
Kalath S, Tsipouras P, Silver FH. Non-invasive assessment of aortic mechanical properties. Ann Biomed Eng, 1986; 14(6): 513-524.
Kalath S, Tsipouras P, Silver FH. Increased aortic root stiffness associated with osteogenesis imperfecta. Ann Biomed Eng, 1987; 15(1): 91-99.
Silver FH, Siperko LM. Mechanosensing and mechanochemical transduction: how is mechanical energy sensed and converted into chemical energy in an extracellular matrix? Critical Reviews™ in Biomedical Engineering, 2003; 31(4): 255-331.
Horvath I, Foran DJ, Silver FH. Energy Analysis of Flow Induced Harmonic Motion in Blood Vessel Walls. Cardiovascular Engineering, 2005; 5: 21-28.
Shah, RG, Silver FH. Viscoelastic behavior of tissues and implant materials: Estimation of the elastic modulus and viscous contribution using optical coherence tomography and vibrational analysis. J Biomed Tech Res, 2017; 3(1): 105-109.
Silver FH, Horvath I, and Foran D. Viscoelasticity of the vessel wall: role of collagen and elastic fibers. Critical Reviews in Biomedical Engineering, 2001; 29: 279-301.
Silver FH, Horvath I, Kelkar N, Deshmukh T, Ruchit Shah. In vivo Biomechanical Analysis of Human Tendon Using Vibrational Optical Coherence Tomography: Preliminary Results, Tomography: Preliminary Results. J Clin Cases Rep, 2020; 4(1): 12-19.
Silver FH, Kelkar N, Desmukh T, Horvath I, Shah RG. Mechano-Vibrational Spectroscopy of Tissues and Materials Using Vibrational Optical Coherence Tomography: a new non-Invasive and non-destructive Technique. Recent Progress in Materials, 2020; 2(2): 1-19.
Silver FH, Shah RG, Silver LL. The use of vibrational optical coherence tomography in matching host tissue and implant mechanical properties. Biomater Med Appl, 2018; 2.
Silver FH, Shah RG, Richard M, Benedetto D. Comparative "virtual biopsies" of normal skin and skin lesions using vibrational optical coherence tomography. Skin Res Tech, 2019; 25: 743-749.

(56) References Cited

OTHER PUBLICATIONS

Silver FH, Shah R. Measurement of mechanical properties of natural and engineered implants. Adv Tissue Eng Regen Med Open Access, 2016; 1, 20-25.
Kinney JH, Gladden JR, Marshall Gea, Marshall SJ, So JH, Maynard JD. Resonant ultrasound spectroscopy measurements of the elastic constants of human dentin. J Biomech, 2004; 37(4), 437-441.

* cited by examiner

SYSTEMS, DEVICES, AND METHODS FOR NON-INVASIVE AND NON-DESTRUCTIVE IMAGING AND MEASUREMENT OF TISSUE AND MATERIAL MECHANICAL PROPERTIES

CROSS REFERENCE TO RELATED APPLICATIONS

The present application claims priority to provisional application No. 62/978,799 filed on Feb. 19, 2020 and the subject matter of provisional application No. 62/978,799 is incorporated by reference herein in its entirety.

FIELD OF THE INVENTION

The present application is directed to systems, devices, and methods for non-invasive and non-destructive imaging and measurement of tissue and material mechanical properties to determine potential disease of the tissue.

BACKGROUND OF INVENTION

Gravity plays a central role in vertebrate development and evolution, tissue repair, and the pathophysiology of disease and regenerative responses. In the presence of a gravitational field, muscular forces required for locomotion or for daily activities are increased (see the following which are incorporated by reference herein in their entireties: (Silver F H (2017) A matter of gravity-mechanotransduction: how mechanical forces influence biological materials. Material Sci & Eng Int J1(20): 00012. DOI:10.15406/mseij.2017.01.00012. Silver F H and Silver L L. Gravity (2017) Mechanotransduction and Healing: How Mechanical Forces Promote Tissue Repair. SM J Biomed Eng. 3(3): 1023. Silver, F. H., Mechanosensing and Mechanochemical Transduction in Extracellular Matrix, Springer, N.Y., 2006. [Silver, 2006 Silver and Silver, 2017; Silver, 2017]. External loading in a gravitational field leads to induction of pathways that modify cell division and protein synthesis [Silver, 2006]). The results of several studies suggest that tissue regeneration, repair, and development of disease changes may in part be stimulated by external mechanical loading and lead to changes in the mechanical properties of cells and tissues (see the following which are incorporated by reference herein in their entireties: Samani A, Bishop J, Luginbuhl C, et al. Measuring the elastic modulus of ex-vivo small tissue samples. *Phys Med Biol.* 2003; 48(14):2183-2198. Samani A, Zubovits J, Plewes D. Elastic moduli of normal and pathological human breast tissues: an inversion-technique-based investigation of 169 samples. *PhysMed Biol.* 2007; 52:1565-1576. Acerbi I, Cassereau L, Dean I, et al. Human breast cancer invasion and aggression correlates with ECM stiffening and immune cell infiltration. *Integr Biol (Camb)*. 2015; 7(10): 1120-1134. Lin H H, Lin H K, Lin I H, et al. Mechanical phenotype of cancer cells: cell softening and loss of stiffness sensing. *Oncotarget.* 2015; 6:20946-20958. Lekka M. Discrimination between normal and cancerous cells using AFM. *Bionanoscience.* 2016; 6:65-80. Emon B, Bauer J, Jain Y, et al. Biophysics of Tumor Microenvironment and Cancer Metastasis: A Mini Review. *Comput Struct Biotechnol J.* 2018; 27(16):279-287. [Samani et al., 2003; Samani et al., 2007; Acerbi et al., 2015; Lin et al., 2015; Lekka, 2016; Emon et al., 2018]).

Many studies have evaluated the effects of mechanical loading at the cellular and tissue levels in vitro; however, few methods are effective in understanding the state of mechanical loading in vivo that is needed to evaluate tissue healing and disease development. Changes in the extracellular matrix (ECM) affect the cell and collagen contents and biomechanics of tissues (see the following which are incorporated by reference herein in their entireties: (Yamada H (1970) Strength of Biological Materials, Williams and Wilkins, Baltimore, USA, pp. 297. Fung Y C (1973) Biomechanics: Mechanical properties of living tissue. ($1^{st}$ edn), Springer-Verlag New York, USA, pp. 568. Dunn M G, Silver F H (1983) Viscoelastic behavior of human connective tissues: Relative contribution of viscous and elastic components. Conn Tis Res 12: 59-70. LaCroix A S, Sarah E. Duenwald-Kuehl S E, Lakes R S, and Ray Vanderby, R Jr. (2013) Relationship between tendon stiffness and failure: a metaanalysis, Appl Physiol 115(1): 43-51, and Silver 2006 [Yamada, 1970; Fung, 1983; Dunn and Silver, 1983; LaCroix et al., 2013; Silver) 2006]). While finite element modeling provides some assistance in interpreting clinical data, many of these studies do not offer information that can be used during a clinical exam to evaluate changes in tissue structure and function. Therefore, it is important to develop a device that will aid in understanding the structure and biomechanical changes that occur in tissues during aging and in diseases and be able to use the device to judge the efficacy of treatments to ameliorate injury and promote healing and to upregulate mechanotransduction needed to treat disease.

Methods for Mechanical Testing of Tissues and Implants

Constant rate-of-strain experiments: Traditionally, tissues and implants have been tested using constant strain-rate experiments where a sample is loaded at a constant rate until failure occurs either in tension or compression. The modulus (E) is obtained from the slope of the stress-strain curve and does not require assuming a value of Poisson's ratio [Yamada, 1970]. The test requires mounting the sample ends in grips and is usually conducted until the sample fails in tension. The determination of the stiffness or modulus requires measurements made at several different levels of the strain. The slope (E) depends on the rate of deformation. As the sample is stretched at a higher rate of strain, the modulus appears to increase because the sample does not have time to relax during deformation. This test can be done in one or more loading directions and can be repeated many times during fatigue tests in tension and compression. The limitations to this test are:

a. The sample is destroyed during testing;
    b. The results need to be corrected for strain-rate dependence;
    c. The modulus can only be evaluated from the slope of the stress-strain curve which requires measurements at several increasing levels of the strain; and
    d. The value of E is difficult to determine from the slope of the stress-strain curve when the slope is rapidly changing.

Incremental stress-strain tests: This test is conducted in tension or compression in a similar manner to constant rate-of-strain methods except the sample is loaded in strain increments [Dunn and Silver, 1983]. After each strain increment is applied to the sample, the sample is allowed to relax under tension or compression until it reaches its final dimensions and the stress is calculated. At that time another strain increment is added and the process is repeated. The data is plotted both as a total stress-strain curve and an elastic stress-strain curve (stress after relaxation has occurred) similar to that done in constant rate-of-strain experiments. The advantage of this method is that the elastic stress-strain curve is not strain-rate dependent. The elastic modulus is obtained from the slope of the stress-strain curve after relaxation has occurred. It turns out that for several collagenous tissues the elastic modulus is strain-rate independent and the elastic component contributes between 50 and 70% to the total stress depending on the degree of orientation of collagen fibers [Dunn and Silver, 1983]. The value of this method is that it gives an elastic modulus value that is a material property (not strain-rate dependent) but the test also requires destruction of the tissue and measurements at increasing strain values. It should be noted that relaxation of the material to equilibrium at each step may require up to 24 hrs. and is a time consuming process.

Contact Manipulation Methods:

Sugimura et al. [2016] (Sugimura K, Lenne P F, Graner F (2016) Measuring forces and stresses in situ in living tissues. Development 143(2): 186-196) review methods for measuring forces and stresses in situ in living tissues by applying physical forces and is incorporated by reference herein in its entirety. The methods require a pushing, pulling, applying light energy, ablation of tissue using lasers, applying liquid droplets and measuring quantities such as the birefringence of anisotropic tissues to evaluate the tissue reaction to applied forces. This approach gives values of local mechanical influences on tissues based on the reaction to applied forces. The results may be difficult to interpret in terms of standard mechanical parameters, such as the modulus, since the measurements are made under local non-equilibrium conditions. The method also requires destruction of the tissue in some cases.

Magnetic Resonance Elastography (MRE):

Low et al. [2016](Low G, Kruse S A, Lomas D J (2016) General review of magnetic resonance elastography. World J Radiol 8(1): 59-72) review the use of magnetic resonance to calculate values of the modulus of tissues, and is incorporated by reference herein in its entirety. In this method, mechanical excitation is produced by pneumatic, electromechanical, or piezoelectric stimulators positioned next to the body. The tissue is loaded by one of these means and then the MRI signal is collected. The phase shift in the MRI signal is used to calculate a value of the modulus; however, the workers assume that Poisson's ratio is 0.5 and that the tissue density is 1.0 g/cc. These assumptions create calculation errors since Poisson's ratio has been shown to vary from 0.5 for tissues. The value of this technique is that it can be used non-invasively in real time; however, use of this technique requires correction for Poisson's ratio and strain-rate effects to be entirely accurate. The advantage of the present invention over MRE is that it is rapid and can be completed in 5 minutes, does not require assuming values of Poisson's ratio, determines an elastic modulus that is not time-dependent, and can be used to measure both surface and internal values of the modulus of the material components, and the present invention can be calibrated. Moreover, Low et al. actually measures a modulus and mechanical property between fibers, rather than the fibers themselves of the tissue to be measured.

Ocular Response Analyzer (ORA):

The ocular response analyzer is a clinical device that uses a high speed air puff to deform the cornea. Changes in shape of the anterior surface are tracked using an infrared beam reflected from the surface and aligned with the geometry of a detector [Ruberti et al., 2014](Ruberti J W, Roy A S, Roberts C J (2014) Corneal biomechanics and biomaterials. Annu Rev Biomed Eng 13: 269-295), which is incorporated by reference herein in its entirety. Using this device corneal deformation is tracked after the air puff is applied to the corneal surface. Differences in the pressures between the inward and outward flattening of the cornea are reported as the corneal hysteresis. Changes in the corneal hysteresis are correlated with disease states anecdotally. The non-invasive measurements made using this device is a positive attribute of this method. However, the inability to relate the results to standard mechanical testing parameters limits the utility of this device.

Oil Microdroplet Deformation:

Campas et al. [2014](Campas O, Mammota T, Hasso S, Sperling R A, O'Connell D, et al. (2014) Quantifying cell-generated mechanical forces within living cells. Nat Methods. 11(2): 183-189, which is incorporated by reference herein in its entirety) describe a method for determining cell-generated mechanical forces within living cells by introducing an oil droplet coated with biologically compatible molecules between cells. These workers use fluorocarbon oils immiscible in vegetable oils and stabilize the droplets using a biocompatible surfactant. The internal tension in the droplet is adjusted to allow measurement of the stresses applied by different types of cells. The geometry of the droplet is related to the local cellular forces through Laplace's Law. Equations are developed that relate the droplet shape in 3D and the anisotropic stresses responsible for inducing the deformation. Oil droplet shape changes are introduced into these mathematical models to calculate intercellular forces and estimate the mechanical interactions that occur in living systems. The problem with this method is that it cannot be used on tissue in vivo.

Optical Coherence Elastography (OCE):

Kennedy et al. [2014; 2014a] (Kennedy B F, Kennedy K M, Sampson D D (2014) A review of optical coherence elastography: fundamentals, techniques and prospects. IEEE Journal of Selected Topics in Quantum Electronics 20(2): 272-288. Kennedy B F, Mclaughlin R A, Kennedy K M, Chin L, Curatolo A, et al. (2014a) Optical coherence microelastography: mechanical-contrast imaging of tissue microstructure. Biomed Opt Express 5(7): 2113-2124), which are incorporated by reference herein in their entireties, have reviewed the use of optical coherence elastography for the analysis of tissue mechanical properties. This technique uses light that is reflected off a surface and compared to the non-reflected light to create an image and to measure displacement after the tissue undergoes a small shear displacement. Mathematical modeling is used to calculate the tissue modulus assuming the tissue is a linear elastic solid and that Poisson's ratio is 0.5. This technique is non-invasive and can be used to evaluate tissue in situ. However, the values of moduli obtained from the models used appear lower than those calculated from destructive testing, suggesting that the strains introduced are not large enough to deform the structural components of the tissue. In addition, this technique can only be applied to surface tissues.

Ultrasound Elastography (UE):

Drakonaki et al. [2012](Drakonaki E E, Allen G M, Wilson D J (2012) Ultrasound elastography for musculoskeletal applications. Br J Radiol 85(1019): 1435-1445), which is incorporated by reference herein in its entirety, point out that ultrasound elastography is referred to by a number of terms including strain elastography, compression elastography, sonoelastography, and real-time elastography. Using these techniques, a low frequency compression is applied to the tissue, frequently via the hand held transducer. The applied compression induces a shear strain and the modulus is estimated from the change in the echo before and after the force is applied. See Zaleska-Low et al. (Zaleska-Dorobisz U, Kaczorowski K, Pawlus A, Puchalskoc A, Inglot M. Ultrasound elastography-review of techniques and its clinical application. Adv Clin Exp Med. 2014; 23: 645-655), which is incorporated by reference herein in its entirety, and which review the use of ultrasound to calculate the modulus values of tissues for different clinical applications. This technique assumes that the tissue is a linearly elastic solid that has a Poisson's ratio of 0.5 and does not measure the modulus directly. The data obtained from UE will depend on the frequency of sound used in the measurements and the assumptions made in converting the displacement to elastic modulus.

Ultrasound devices equipped with a sonoelastography option enable more accurate imaging and evaluation of the nature of lesions situated at small depths beneath the tissue surface in breast, thyroid, testicles, prostate and some groups of lymph nodes [Zaleska et al., 2014]( Zaleska-Dorobisz U, Kaczorowski K, Pawlus A, Puchalskoc A, Inglot M (2014) Ultrasound elastography-review of techniques and its clinical application. Adv Clin Exp Med 23(4): 645-655, which is incorporated by reference herein in its entirety).

Surface Waves and Optical Coherence Tomography (OCT):

Li et al. [2012](Li C, Guan G, Huang Z, Johnstone M, Wang R K (2012) Noncontact all-optical measurement of corneal elasticity. Opt Lett 37(10): 1625-1627, which is incorporated by reference herein in its entirety) report creation of a surface wave in the cornea and evaluation of the mechanical properties using surface wave velocity measurements. They use pulsed laser excitation to create a surface wave and estimate the modulus from an equation that relates the surface wave velocity to the modulus. Song et al. [2015](Song S, Le N M, Huang Z, Shen T, Wang R K (2015) Quantitative shear-wave optical coherence elastography with a programmable phased array ultrasound as the wave source. Opt Lett 40(21): 5007-5010, which is incorporated by reference herein in its entirety) use ultrasound to create a shear wave and used OCE to measure the properties of tissue. The above studies assumed a value for Poisson's ratio and a density to calculate the mechanical properties. The assumption of a value of 0.49 for Poisson's ratio leads to calculation errors as discussed above. Again with OCT only the surface tissues can be evaluated.

Shah et al. [2016](Shah R, Pierce M C, Silver F H (2016) A method for non-destructive mechanical testing of tissues and implants. J Biomed Mater Res A, which is incorporated by reference herein in its entirety) used vibrational analysis in concert with OCT to measure the natural frequency of decellularized dermis and silicone rubber. They applied an acoustic vibration to the samples under tension and showed that the natural frequency squared obtained from the change in frequency of the reflected light was directly related with the tensile modulus obtained in an incremental stress-strain experiment. Moduli from vibrational analysis compared very well to moduli obtained from incremental stress-strain curves. Their method did not rely on the assumption of a value of Poisson's ratio; however, their method was only able to measure the modulus of surface tissue including skin.

Non-destructive and non-invasive characterization of tissues and implants has been an important goal for researchers for decades. Unfortunately, the use of ultrasound and elastography provide only estimates of the exact values of mechanical parameters such as the modulus. OCE has been recently applied to studying tissue properties in health and disease; however, the values reported for tissue moduli are in the KPa range [Kennedy et al., 2014, 2014a] as opposed to the MPa range that is expected for biological polymers [Dunn and Silver, 1983; Shah et al., 2016]. Several diseases such as connective tissue disorders and cancer formation are characterized by changes in the mechanical properties such as modulus and hardness. See the following references which are incorporated herein in their entireties: (Kalath S, Tsipouras P, Silver F H (1986) Non-invasive assessment of aortic mechanical properties. Ann Biomed Eng 14(6): 513-524. Kalath S, Tsipouras P, Silver F H (1987) Increased aortic root stiffness associated with osteogenesis imperfecta. Ann Biomed Eng 15(1): 91-99, [Kalath et al., 1986, 1987]), and see also Samani et al., 2003, 2007; Acerbi et al., 2015; Lin et al, 2015; Lekka, 2016]. It is important to be able to accurately calculate the value of the modulus since it depends on the exact composition of the macromolecular components, their orientation and the degree of cross linking of the components [Silver, 2006].

A number of methods and devices have been described in the patent literature. Sarvazyan, U.S. Pat. No. 5,606,971, which is incorporated by reference herein in its entirety, describes the use of a focused ultrasonic wave and a liquid coupling gel to detect shear waves in a material. This patent discusses use of shear waves to determine the tissue modulus but does not indicate how the modulus can be calculated without making several assumption such as Poisson's ratio or how the technique is calibrated. In addition, it uses a liquid coupling agent and therefore the agent must touch the tissue to be studied.

Melese et al., U.S. Pat. No. 7,477,571 B2, which is incorporated by reference herein in its entirety, describes use of electromagnetic radiation reflected or emitted from a biological organism to provide real-time imaging of a target object. However, they fail to describe how the emissions can be converted into a tissue modulus and how the measurement can be calibrated.

Fatemi et al., U.S. Pat. No. 9,345,448 B2, which is incorporated by reference herein in its entirety, use pressure waves to produce shear elastic modulus maps of tissues but they fail to state either how their technique is calibrated or how they can calculate a modulus without determining Poisson's ratio. They also imply that they can determine viscoelasticity without clearly providing evidence of the ability of the method to separate elastic and viscous contributions to the modulus. Their use of waves that create a shear displacement of the surface of a material does not provide information concerning the mechanical properties of the inner components. Fatemi et al., fails to provide information on all the components of the material.

Larin et al., US Patent Application Publication 2017/0290503, which is incorporated by reference herein in its entirety, use optical coherence elastography and pulsed air to detect the progression of ocular and other degenerative diseases. However, their method only reports values of Young's modulus in the KPa range as opposed to the MPa range reported for the cornea measured in vitro. The use of an air puff applied to the cornea also introduces the problem of how to determine the exact pressure applied to the tissue and how to prevent the introduction of contaminants to the eye. As reported previously, values of the modulus measured using shear waves underestimate the actual moduli determined using tensile testing.

Chen et al., US Patent Application Publication 2019/03359996A1, which is incorporated by reference herein in its entirety, describe the use of shear wave acoustic radiation force optical coherence elastography. They use an ultrasound transducer to apply shear waves to measure the wave propagation through ocular tissues. The use of shear waves propagating through a medium provides an image but does not provide an accurate modulus measurement.

Silver et al., U.S. Pat. No. 10,488,277, which is incorporated by reference herein in its entirety, teach that tissue or material stiffness can be determined by applying a longitudinal wave or pressure wave to a tissue or material and measuring the frequency of the applied vibration that causes the maximum displacement of the tissue. The stiffness (modulus) is determined from a calibration curve. While they provide a method for measuring the modulus of a bulk material or tissue surface they do not teach how images and measurement of the stiffness can be made internal to tissues beneath the skin or internal to a material. In addition, they do not describe how stiffness measurements can be made on internal material structures where stress concentrations or cracks may occur.

What is needed is a way to measure tissues in vivo, safely, and quickly, and in a way that provides an image and measurement of the modulus of internal tissues and material structures.

SUMMARY OF THE INVENTION

In an embodiment, the present invention is directed to a system including a first device configured to utilize electromagnetic waves to determine a modulus of a portion of bulk material or subcutaneous tissue, and a second device operably connected to the first device and configured to generate induced vibrations. The first device may be configured to determine the modulus of the bulk material or subcutaneous tissue through reflected vibrations reflected from the bulk material or subcutaneous tissue to an outer surface of the bulk material or subcutaneous tissue. The first device may be an optical coherence tomography device.

In another embodiment of the present invention, the induced vibrations may be sound vibrations or other mechanical vibrations. The second device may be a device configured to produce audible sound, a device configured to produce electrical fields, or a device configured to produce magnetic fields. The induced vibrations may have frequencies of between 30 and 20,000 hertz.

In another aspect of the invention, the first device is configured to determine the resonant frequency of the bulk material or subcutaneous tissue. The second device imposes vibrations that may be sinusoidal audible sound vibrations with variable frequency as a function of time. A third device (a second imaging component in addition to the first device) may be an ultrasound device, an NMR device, a positron emission tomography device, an x-ray device or a photography device to find the spot for where the first device (e.g, OCT) is used. The second device may be positioned such that the imposed/induced first vibrations are at least partially transverse to the outer surface. Preferably, the amplitudes of the induced vibrations extend at least 50% transversely to the outer surface.

In an aspect of the invention, the induced vibrations are configured to vibrate the bulk material or subcutaneous tissue, and the first device is configured to determine the resonant frequency of the bulk material or subcutaneous tissue by measuring reflected light from the bulk material or subcutaneous tissue vibrated by the induced vibrations. The first device may be configured to emit first signals to the outer surface and to detect second signals from the outer surface. The first signals and the second signals preferably are at least 50% coherent with one another.

In an aspect of the invention, the first device is configured to determine the resonant frequency by measuring displacement of the bulk material or subcutaneous tissue as a function of the frequency or time of the induced vibrations. Additionally, the first signals and the second signals can be in the visible spectrum or of any other wavelength.

In the present invention, the system may be configured to conduct at least one selected from the group consisting of: evaluating vessel wall thickening, aging, athero- and arteriosclerosis of the vessel walls and structures of the cardiovascular system; determining the degree of injury to a subcutaneous tissue based on changes in the tissue stiffness; evaluating the efficacy of treatment to improve wound healing or ameliorate disease of skin; evaluating the efficacy of treatments to alter the effects of aging of skin; evaluating the deposition of fat and fibrosis of the liver; evaluating the deposition of lipid and mineral or aneurysms that lead to stenosis or dissection of arteries, lymphatics or veins; evaluating tissue dysplasia and fibrosis of reproductive tissues in women and testes in males; evaluating the urinary and digestive tracts in males and females; evaluating lung fibrosis, esophageal changes and mucin deposition in the airways; evaluating heart septal defects, valvular stenosis and ventricular hypertrophy; evaluating pulmonary artery insufficiency; evaluating muscular atrophy, fibrosis and tissue damage; evaluating nerve crush injuries and the results of nerve entubulation repairs; evaluating the repair of tendons and ligaments using autografts and allografts; evaluating normal and diseased ocular tissues including lens, cornea, sclera, retina, lamina cribosa and optic nerve; evaluating stress fractures in bone and cranium; evaluating tears and evulsions of tendons and ligaments; evaluating the efficacy and degradation rates of implanted medical devices evaluating the biological compatibility, irritation, reactivity and the lifespan of implants in animals; evaluating the cell density and protein deposition of cell and tissue components in tissue cultures; evaluating cartilage in joints and ear; evaluating the repair of tendons, vessels, joint components and ligaments in the hands, joints and feet; evaluating bacterial and viral contamination, infection and healing of wounds and skin ulcers; evaluating fat deposition and fibrosis in the liver; evaluating blood smears and tissue aspirates; evaluating kidney function and fibrosis; evaluating bone, perichondrium and periosteum as a source of growth factors, stem cells or tissue transplants; evaluating breast tissue or breast biopsies for the presence of fibrosis, cancerous tumors and calcifications; evaluating the prostate, thyroid and lymph nodes; evaluating skin lesion, cancers, inflammation and other proliferative diseases. This is done by measuring the modulus and comparing it to a standard for the particular tissue being evaluated.

In another aspect, the present invention is directed to a method of determining the resonant frequency of bulk material or subcutaneous tissue comprising: vibrating an outer surface of the bulk material or subcutaneous tissue with induced vibrations having varying frequencies as a function of time to vibrate the bulk material or subcutaneous tissue and determining displacement of the outer surface with electromagnetic waves to determine the resonant frequency of the vibrating outer surface. The method may also include determining a modulus of the bulk material or subcutaneous tissue. Determining of the displacement of the outer surface may be conducted with an optical coherence tomography device. The induced vibrations may be sound vibrations or other mechanical vibrations. The induced vibrations may be generated with a device configured to produce audible sound, a device configured to produce electrical fields, or a device configured to produce magnetic fields. Preferably, the induced vibrations have frequencies between 30 and 20,000 hertz. Also, preferably, the induced vibrations comprise a sinusoidal audible sound vibrations.

In an aspect of the invention, the induced vibrations are configured to be at least partially transverse to the outer surface. Preferably, the amplitudes of the induced vibrations extend at least 50% transversely to the outer surface.

In an aspect of the present invention, determining the resonant frequency of bulk material or subcutaneous tissue includes using an ultrasound device, an NMR device, a positron emission tomography device, an optical coherence tomography device, an x-ray device, or a photography device to locate the area of skin to be vibrated and/or the area of skin where vibrations will be measured. Also, determining displacement of the outer surface may include measuring reflected light from the bulk material or subcutaneous tissue vibrated by the induced vibrations. Determining displacement of the outer surface may include emitting first signals to the outer surface and detecting second signals from the outer surface, and where the first signals and the second signals are at least 50% coherent with each other. Also, determining displacement of the outer surface may include determining displacement of the bulk material or subcutaneous tissue as a function of the induced vibrations. Additionally, the reflected light can be in the visible spectrum or any other wavelength.

In another embodiment the present invention is directed to a method to determine the spectra of resonant frequencies of subdermal tissues including: applying a sinusoidal audible sound wave or any other mechanical excitation to the surface of skin and collecting the spectra of resonant frequencies reflected from internal tissues.

In one aspect, the system includes a first device configured to utilize electromagnetic waves to determine a modulus of a portion of bulk material or subcutaneous tissue, and a second device operably connected to the first device and configured to generate induced vibrations. The first device and the second device may be operably connected to each other and are part of a same piece of equipment or are separate pieces of equipment and the first device may be configured to (A) determine a modulus of the bulk material or subcutaneous tissue through reflected vibrations reflected from the bulk material or subcutaneous tissue to an outer surface of the bulk material or subcutaneous tissue and/or (B) determine a resonant frequency of vibrations of the bulk material or subcutaneous tissue. The first device may be configured to receive frequency data from the second device and to process such frequency data to (A) determine the modulus of the bulk material or subcutaneous tissue through the reflected vibrations reflected from the bulk material or subcutaneous tissue to the outer surface of the bulk material or subcutaneous tissue and/or (B) determine the resonant frequency of vibrations of the bulk material or subcutaneous tissue.

In another aspect, the first device comprises one or more processors and one or more data storage devices, and a first of the data storage devices stores the frequency data and wherein the first or a second of the data storage devices comprises instructions stored therein, which when executed by the one or more processors, cause the one or more of the processors to perform operations including processing of the frequency data.

The first device may be an optical coherence tomography device and the induced vibrations may be sound vibrations or other mechanical vibrations. The second device may be a device configured to produce audible sound, a device configured to produce electrical fields, or a device configured to produce magnetic fields.

The induced vibrations may have frequencies of between 30 and 20,000 hertz, and the induced vibrations may include sinusoidal audible sound vibrations with variable frequency as a function of time. The second device may include a piezoelectric device or a speaker (e.g. a diaphragm speaker).

In an embodiment, the second device is configured such that the induced vibrations extend at least 50% transversely to the outer surface. Furthermore, the first device may be configured to emit first signals to the outer surface and to detect second signals from the outer surface, where the first signals and the second signals are at least 50% coherent with one another. The first device can be configured to determine the resonant frequency by measuring displacement of the bulk material or subcutaneous tissue as a function of the frequency or time of the induced vibrations.

In an aspect of the present invention, the modulus is determined based on a thickness of the skin as well as on the resonant frequency. The modulus may be directly related to the square of the resonant frequency and inversely related to the thickness of skin. The modulus may be determined in accordance with the following equation in which E is the modulus, d is the thickness of skin in meters, and f is the resonant frequency in Hertz of the induced vibrations:

$$E = 0.0654 * \frac{f^2}{d} + 233160$$

In another embodiment, the modulus or resonant frequency are determined by measuring displacement of skin tissue included by the outer surface of subcutaneous tissue, in a direction perpendicular to the outer surface of the subcutaneous tissue. The modulus or resonant frequency may be determined by measuring displacement of skin tissue encompassed by the outer surface of the subcutaneous tissue, at a fixed location of the skin tissue.

In an embodiment of the present invention, the second device comprises a speaker. In another embodiment, the first device is an optical coherence tomography device and the second device is a speaker configured to produce audible sound waves.

In yet another embodiment, a system includes an optical coherence tomography device configured to receive frequency data and configured to measure displacement of skin tissue to generate displacement data. The system may further include one or more processors and one or more data storage devices with instructions stored therein, which when executed by the one or more of the processors, cause the one or more of the processors to perform operations including processing of the frequency data and the displacement data to determine a modulus.

The present invention may also be directed to a method of determining (A) a modulus of bulk material or subcutaneous tissue through reflected vibrations reflected from the bulk material or subcutaneous tissue to an outer surface of the bulk material or subcutaneous tissue and/or (B) a resonant frequency of vibrations of the bulk material or subcutaneous tissue. Such method may include vibrating the outer surface of the bulk material or subcutaneous tissue with induced vibrations having varying frequencies as a function of time to vibrate the bulk material or subcutaneous tissue and determining displacement of the outer surface with electromagnetic waves, and utilizing the frequencies of the induced vibrations and the displacement of the outer surface to determine the modulus and/or the resonant frequency.

In an aspect of the invention, a system includes a first device configured to utilize electromagnetic waves to determine a resonant frequency of induced vibrations modulus of at least one component a portion of bulk material or subcutaneous tissue, and a second device is operably connected to the first device and configured to generate the first induced vibrations. The first device and the second device are operably connected to each other and are part of a same piece of equipment or are separate pieces of equipment. The at least one component of bulk material or subcutaneous tissue can include a plurality of components of bulk material or subcutaneous tissue and the resonant frequency of each of the plurality of bulk material or subcutaneous tissue is determined from a single spectrum of the induced frequencies. The modulus of each of the plurality of bulk material or subcutaneous tissue can also be determined from a single spectrum of the induced frequencies.

BRIEF DESCRIPTION OF THE DRAWINGS

Features and advantages of the invention will be apparent from the following, more particular description of various embodiments, as illustrated in the accompanying drawings wherein like reference numbers generally indicate identical, functionally similar, and/or structurally similar elements.

FIG. 1b shows an enlarged portion of FIG. 1a.

DETAILED DESCRIPTION

Figure 1A:
FIG. 1a is directed to a schematic showing various tissues on a human body.

The detailed description set forth below is intended as a description of some, but not all, of the configurations of the subject technology and is not intended to represent an exhaustive list. The detailed description includes specific details for the purpose of providing a thorough understanding of the present invention and subject technology. The subject invention and technology is not limited to the specific details set forth herein and may be practiced without these specific details. In other instances, well-known structures and techniques have not been shown in detail so as not to obscure the disclosure. Exemplary embodiments are discussed in detail below. While specific exemplary embodiments are discussed, it should be understood that this is done for illustration purposes only. In describing and illustrating the exemplary embodiments, specific terminology is employed for the sake of clarity. However, the embodiments are not intended to be limited to the specific terminology so selected. A person skilled in the relevant art will recognize that other components and configurations may be used without parting from the spirit and scope of the embodiments. It is to be understood that each specific element includes all technical equivalents that operate in a similar manner to accomplish a similar purpose. The examples and embodiments described herein are non-limiting examples.

All publications cited herein are hereby incorporated by reference in their entirety. As used herein, the term "a" refers to one or more. The terms "including," "for example," "such as," "e.g.," "may be" and the like, are meant to include, but not be limited to, the listed examples. The present invention overcomes the limitations of previously described devices that fail to provide an image and measurement of the modulus of internal tissues and material structures. The present invention overcomes these drawbacks by providing a system (otherwise referred to as a "device") and method that non-invasively and non-destructively provides an image and absolute value of the modulus as well as a spectrum of the moduli internal to a tissue or material. The present invention relates to systems, devices, and methods for evaluating tissue structure and determination of the mechanical properties of normal and diseased tissues in order to optimize the treatment to ameliorate these conditions. The devices allow for the differentiation of normal tissue structure and mechanical properties and changes that are associated with disease and medical treatments.

An embodiment of the invention is the use of a linear piezoelectric probe and high frequency ultrasound to image tissues such as tendon, muscle, cartilage, bone, vessel, and nerve, and then measure at the location defined from the ultrasound image the spectra of resonant frequencies observed at the skin surface from reflected audible sound waves using optical coherence tomography. In the present application, the term "resonance frequency" and "resonant frequency" shall be interchangeable.

The present invention provides devices and methods that can be used for early evaluation and more frequent follow-ups of patients who experience bladder, lymph node, breast, testicular, muscle, prostate, cartilage, bone, cardiovascular, heart, cranial, neurologic, dental or other internal tissue changes associated with diseases or implantable materials. In addition, the devices can be used to follow the amelioration of injury or damage to a tissue as well as a method to evaluate the efficacy of treatments to tissues and organs that are injured or diseased. It also provides a method to evaluate how mechanical forces promote healing of a variety of tissues external and internal to the body.

The device may use optical coherence tomography and audible sound in combination with a secondary imaging technique, such as ultrasound to determine the location of the tissue, that provides an image of internal structures. It can also be used with other secondary imaging techniques including X-rays, photographs, CT scans, MRI or positron-emission tomography to determine the location of the tissue to be analyzed in lieu or in addition to the ultrasound. The frequency response of each tissue component is analyzed by measuring the frequency at which the maximum displacement of each component is observed. The surface vibrations are produced by application of a surface vibration (e.g., via a surface pressure wave) causing a tissue deflection perpendicular to the tissue surface in the skin.

For instance, the Achilles tendon is one example of a location for the use of the device and technique. The device may use ultrasound to image the Achilles tendon and determine where it is and then in conjunction with optical coherence tomography and vibrational analysis the resonant frequency and modulus are determined based on analysis of the vibrations that are reflected back to the skin surface. The resonant frequency can be measured using optical coherence tomography or any other technique that can measure skin vibrations in the 30 to 20,000 Hz range. Other techniques to measure these vibrations include mechanical and electronic devices that can respond to these frequencies. Using low frequency spectral analysis of biological tissues is expected to result in the characteristic physical mechanical properties which can be directly inferred from this frequency spectrum.

The foregoing and other aspects and advantages of the invention will appear from the following description. In the description, reference is made to the accompanying drawings that form a part thereof, and in which there is shown by way of illustration a preferred embodiment of the invention. Such embodiment does not necessarily represent the full scope of the invention, however, and reference is made therefore to the claims and herein for interpreting the scope of the invention.

One embodiment of the invention involves using ultrasound (or any other imaging technique that provides an image of tissues on or below the surface of the body or even blood samples or tissue biopsies or aspirates.) to determine the location of the desired tissue. Then, optical coherence tomography in conjunction with vibrations can be used to determine images and mechanical properties, including a frequency spectral image of mechanical properties. In essence, the ultrasound (or other secondary imaging component) can be used to find the location of structures that are to be measured. For example, if one is interested in a blood vessel, one can find it with the ultrasound and then can find a place on the skin which is directly opposite/above to where the tissue of interest is. The images and mechanical properties may be obtained through use of the devices shown in FIG. 4 and analysis of vibrations resulting from vibrating imaged tissue. Applying audible sound or mechanical vibrations that causes skin movement of various degrees provides a means to generate a frequency spectrum from the reflection of the vibrations back to the skin from the underlying tissues. The minimum frequency of the vibration(s) that causes the maximum deflection(s) of each tissue component is defined as the resonant frequency of each tissue component. The resonant frequencies and moduli of the tissue components are then used to identify tissue injury or the extent of tissue healing.

In a first aspect of the present invention, a device is used to produce an image (e.g., a spectral image) of the desired structure on the surface of the skin directly above the tissue or organ to be evaluated in addition to an image of the tissue or organ to be evaluated. In another aspect of the present invention, an ultrasound image is obtained using a linear piezoelectric probe operating at frequencies between 5 and 75 MHz (see FIG. 3). While ultrasound has been used for decades to obtain low contrast images of many tissues, the advent of high frequency ultrasound has improved the images of tissues beneath the surface of skin. The ultrasound probe used may be a linear probe with a maximum depth of 80 mm and with a center frequency of 7.5 MHz. Linear probes are a high frequency probe capable of generating high resolution images of structures near the body surface. This makes it an ideal probe for imaging vascular structures and other structures below the skin. Along with proving better resolution images, linear probes also provide a flat and regular surface which increases the field of vision as compared to sectorial probes. Once the image is obtained of the tissue in the example, such as the Achilles tendon, the surface of the skin is marked where the image was collected.

Figure 1B:
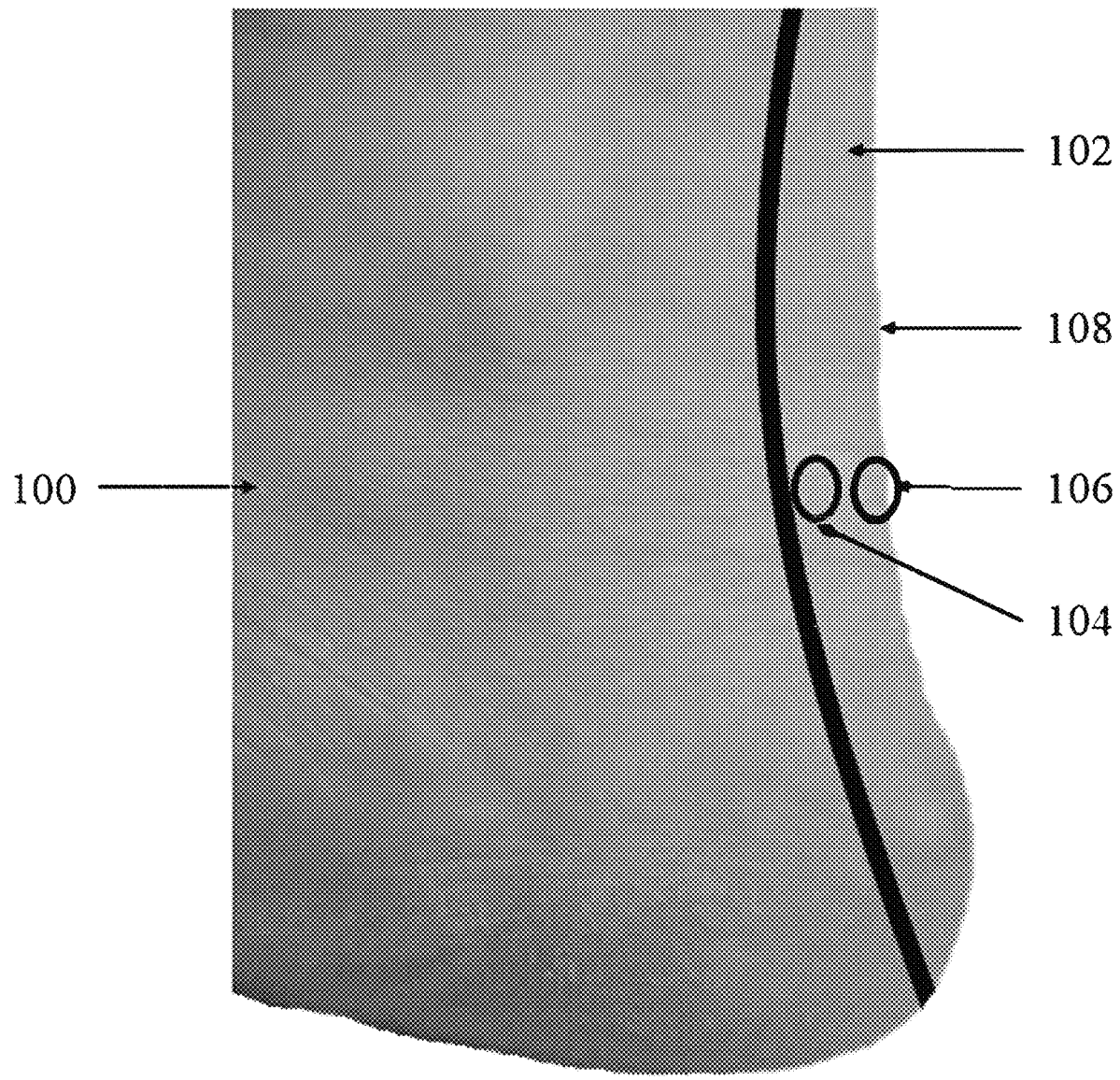
Figure 3:
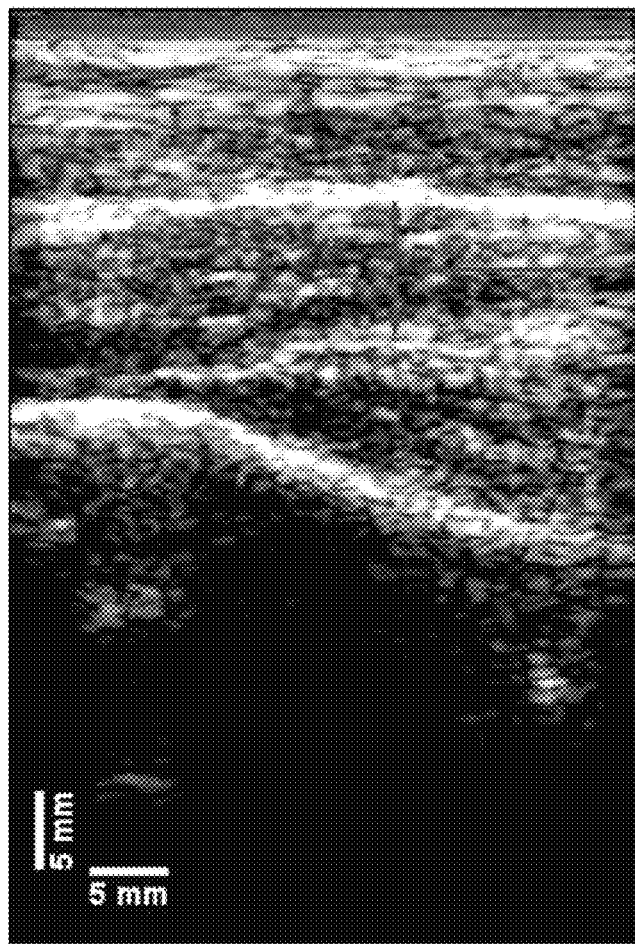
FIG. 3 shows an ultrasound image of an Achilles tendon.

The image may be that of an Achilles tendon, and the surface of the skin is marked where the image was collected and the hand piece of the optical coherence tomography (OCT) unit may be placed above the marked area of skin. FIG. 1a shows an example of a foot 100 of a subject, and an Achilles tendon 102. FIG. 1b shows an enlarged portion of FIG. 1a. An ultrasound image may be taken of the Achilles tendon 102 and then, based on that, the tissue to be analyzed 104 is identified and a surface marking 106 is made on the skin 108 corresponding to the tissue 104. Thus, ultrasound is utilized to determine the tissue to be analyzed 104 and to locate a portion on the skin 108 that corresponds to that tissue. FIG. 3 shows an ultrasound image of a human Achilles tendon using a linear ultrasonic probe. The white (horizontal) arrow illustrates the location of the tendon while the red (vertical) arrow illustrates the width of the Achilles tendon.

Figure 2:
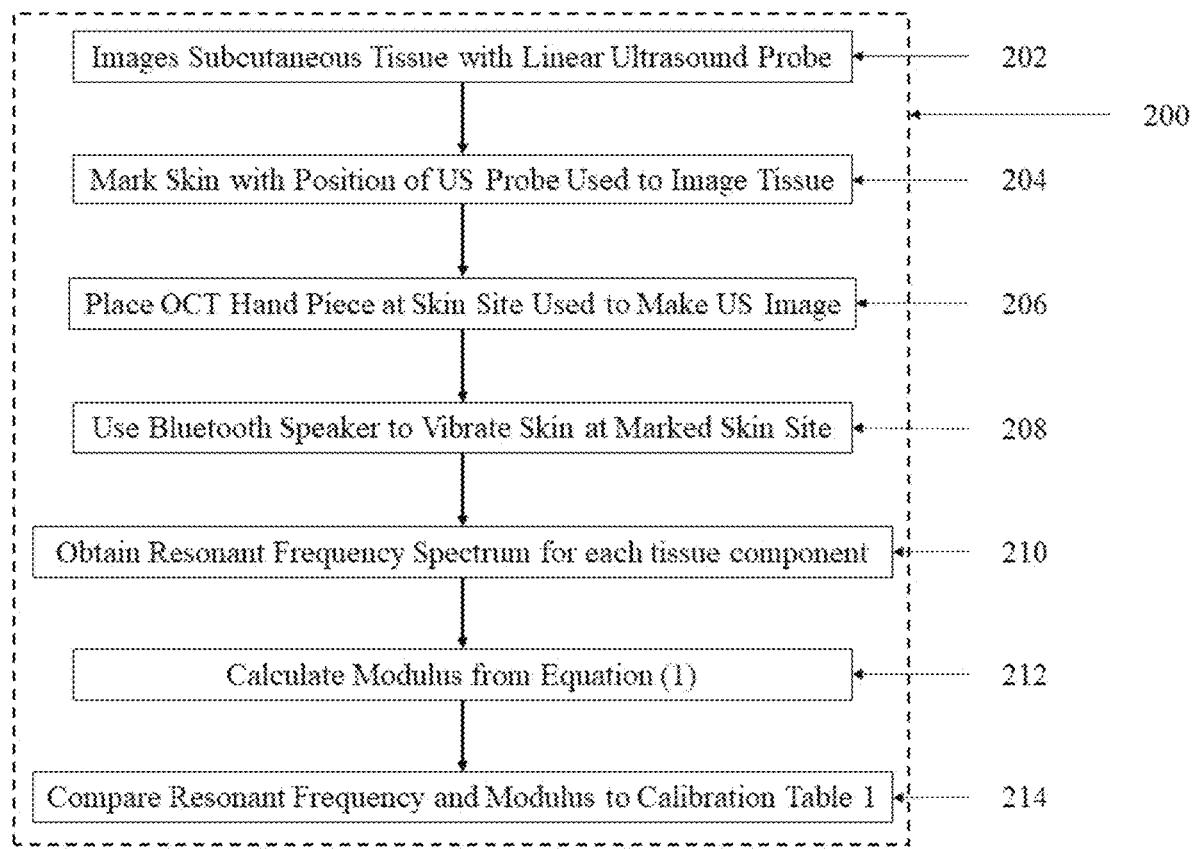
FIG. 2 shows a process flow diagram which reflects the steps of an embodiment of the present invention.

FIG. 2 shows a diagram of a process 200 of the steps involved in imaging and measuring the modulus of a subcutaneous structure where the first step 202 is to image the subcutaneous tissue with a linear ultrasound probe. Such subcutaneous tissue would include tissue 104 in FIG. 1b. Then step 204 involves using the information from the ultrasound probe to mark the skin corresponding to the tissue.

Figure 7:
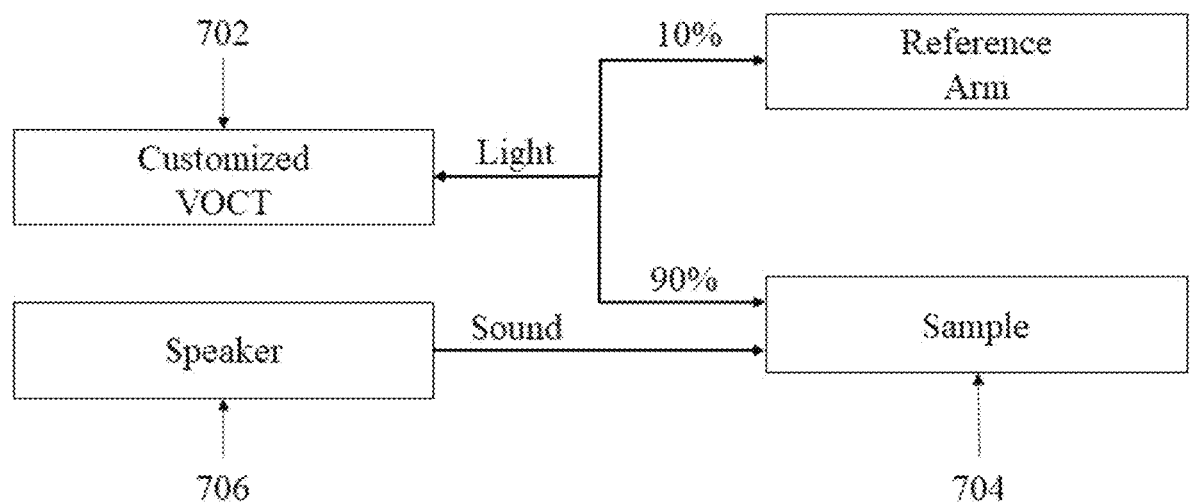
FIG. 7 shows a diagram of the interactions between a VOCT and a speaker in an embodiment of the present invention.

An aspect of the present invention involves determining the weighted displacement versus frequency of the skin above the Achilles tendon being measured from the change in the instantaneous skin tissue thickness measured from the raw OCT image. This corresponds to steps 206, 208, and 210 at FIG. 2. The tissue thickness changes due to the vibrations imparted to the skin by, for example, a speaker. The hand piece of the OCT unit is placed above the marked area of skin. A schematic diagram of the OCT unit with sound applied by a speaker is shown in FIG. 7. A wireless speaker 706 can be placed above the skin and a longitudinal sound wave is directed at the skin surface as shown at FIG. 7. The VOCT 702 at FIG. 7 is a modified OCT which can process vibration frequency data from an external source such as a speaker.

Step 206 involves placing a hand piece on the marked skin 106 (see FIG. 1b). Step 208 involves the use of a wireless speaker to vibrate skin at the marked skin 106. In order to cause this vibration, the speaker is placed near the marked skin, such as one inch or so above skin near the marked skin 106 and is turned on to emit sound. Cutaneous displacement is generated using sinusoidal audible sound by placing the wireless activated speaker over the skin above the area to be studied. Sinusoidal sound waves are generated using a tuning application available on the internet. The speaker could be near (such as next to) the OCT hand piece and does not touch the OCT hand piece. The speaker provides a sinusoidal sound wave at a fixed frequency. The frequency is automatically increased after the data is collected by the computer that is interfaced to the OCT. Thus, the wireless speaker is used to vibrate skin at frequency A. Then, the VOCT determines the displacement of the tissue at frequency A. The wireless connection frequency of the speaker does not interfere with the measurement frequency. Then, the wireless speaker is used to vibrate skin at frequency B and the VOCT determines the displacement of the tissue at frequency B. Thus, audible sound is used to vibrate the tissue at different frequencies. The displacement of the skin by applying audible sound causes vibrations in subcutaneous tissues that are reflected back to the skin and these are measured by the OCT. Thus, the optical coherence tomography and the audible sound can be applied to the tissue (sample 704) as shown at FIG. 7. In the present application, a reference to an OCT encompasses a reference to a VOCT since a VOCT is a specific way in this application of describing an OCT with additional functionalities, namely, the ability to process raw unaveraged frequency data of a spectral image.

In the present invention, the speaker may be operably connected to the OCT such that the displacement determined by the OCT can be matched with the frequency which is created by the speaker. In such a case, if the speaker operates at a frequency of, for example, 200 hertz, the OCT would measure displacement and the system would match the displacement measured by the OCT with the frequency of the speaker. The OCT and the speaker would be operably connected in that they would be operating at the same time. In Step 210 of FIG. 2, the spectrum of resonant frequencies are recorded by measuring the displacement of the skin (from the vibrations) as a function of frequency (known as spectral image) from the displacement of the skin from the transverse sound wave measured from the raw image of the position of the skin (as opposed to the summed image characteristic of most OCT images). A schematic diagram of the OCT unit with sound applied by a speaker 706 is shown in FIG. 7.

The system can measure tissue or can measure physical properties of non-tissue material, such as polymers. Also, the device that generates the vibrations could be a speaker or a different vibration generator. Similarly the device that measures the movement of the tissue or non-tissue material can be an OCT or other device. In general, the system includes a first device configured to utilize electromagnetic waves to determine a modulus of a portion of bulk material or subcutaneous tissue, and a second device operably connected to the first device and configured to generate induced vibrations. The first device and the second device are operably connected to each other and are part of a same piece of equipment or are separate pieces of equipment and the first device is configured to (A) determine a modulus of the bulk material or subcutaneous tissue through reflected vibrations reflected from the bulk material or subcutaneous tissue to an outer surface of the bulk material or subcutaneous tissue and/or (B) determine a resonant frequency of vibrations of the bulk material or subcutaneous tissue (e.g., from a spectral image).

In the present application, the meaning of an "outer surface" of the bulk material or subcutaneous tissue means the "surface" of such bulk material or tissue which faces the OCT or other device which is measuring displacement, such as the skin which faces the OCT device and which corresponds to the subcutaneous tissue to be measured by being aligned with such subcutaneous tissue. Thus, the meaning of "outer surface" in the present application means the outermost surface (i.e., the interface with the air).

The first device which is part of the system is configured to receive frequency data from the second device and to process such frequency data to (A) determine the modulus of the bulk material or subcutaneous tissue through the reflected vibrations reflected from the bulk material or subcutaneous tissue to the outer surface of the bulk material or subcutaneous tissue and/or (B) determine the resonant frequency of vibrations of the bulk material or subcutaneous tissue. For example, if the first device is an OCT device and the second device is a wireless speaker, the frequency data from the speaker would be inputted into the OCT device and this would be the frequency data used by the speaker. In the present application the frequency of vibrations of the actual tissue or bulk material is not measured or calculated and the frequency of the vibration device, such as the wireless speaker, is imputed as the frequency of vibration of subcutaneous tissue or bulk material. In other words, the term "induced vibrations" in the present application is a reference to the vibrations which are generated by the wireless speaker or other vibration generating device, as well as the vibrations of the tissue which are induced by the wireless speaker or other vibration generating device since the vibrations generated by the wireless speaker or other vibration device and induced into the tissue are imputed to be the same and have the same frequencies. Thus, if a wireless speaker generates a sound wave of 1000 Hertz, such 1000 Hertz will also be imputed as being the frequency of the vibration of tissue exposed to such sound wave. Thus, the reference to "induced vibrations" is a reference to what is generated by the vibration device as well as what occurs to tissue or bulk material when exposed to vibrations generated by a vibration device. Any reference to the "frequency" of subcutaneous tissue or skin or bulk material is, in essence, a reference to the frequency of the device that is vibrating the subcutaneous tissue, or skin or bulk material such as the frequency of sound waves from a speaker. Thus, if a resonance frequency is 1000 Hertz, this is not necessarily the actual vibrational frequency of the tissue, rather this would be the vibrational frequency of the vibrations generated by, for example, the speaker. Thus, the resonant frequency of a tissue or bulk material in the present application is meant to refer to the applied frequency at which the maximum displacement is observed for each tissue component (or bulk material). This is the reason why it's important for the OCT or other device to be operably connected to the speaker or other device, since the frequencies are going to be imputed from the speaker or other device as opposed to calculated from the actual movement of skin or other material.

The OCT or other device that measures displacement includes one or more processors and one or more data storage devices. A first of the data storage devices stores the frequency data (e.g., the frequency data from the speaker which is imputed as the frequency of the skin or other material vibrations) and the first or a second of the data storage devices comprises instructions stored therein (e.g., software), which when executed by the one or more of the processors (such as a processor in a computer), cause the one or more of the processors to perform operations including processing of the frequency data. The frequency data is processed by the OCT or other device and when this is processed in combination with the change in displacement of the skin or other material (as determined by the OCT device), the result is the determination of the resonant frequency and/or modulus.

The measurement by the OCT or other device is preferably done transversely to the skin (i.e., perpendicular to the surface of the skin). Thus, preferably, the device that generates the vibrations is configured such that the vibrations extend at least 50% transversely to the outer surface of tissue or other substance to be vibrated. This will, in turn, vibrate the tissue or other substance at least partially orthogonally in order to have orthogonal displacement relative to the surface of the skin or other material. This is explained in more detail below.

Thus, in an aspect of the invention, the system is structured such that the OCT or other device is configured to determine the resonant frequency by measuring displacement of the bulk material or subcutaneous tissue as a function of the frequency or time of the vibrations by the speaker or other device. The system is configured such that measuring displacement of skin tissue comprised by the outer surface of the subcutaneous tissue, is done at a fixed location of the skin tissue. Thus, the OCT or other device can measure displacement of skin or other material in one location rather than measuring at multiple locations and having to add the various measurements at different locations.

In another aspect of the invention, the system is configured to convert the measured resonant frequencies into modulus values using equation (1). This is shown at FIG. 2 as step 212. The resonant frequency f and thickness d are used in Equation 1 to determine the modulus E. This can be done by the OCT device or separately. The modulus, E, is computed from the frequencies, f, at which the maximum displacements of the tissues are observed in the skin. When the skin is vibrated, the resonant frequency of both the Achilles tendon and skin will be measured/calculated from the secondary vibrations seen in the skin that are reflected back from the internal tissues. Thus, the modulus E is calculated using Equation 1 where d is the skin tissue thickness in meters and E is in Pascals and f is in Hertz. This is an empirical equation and the resulting number is deemed to be in Pascals.

$$E = 0.0654 * \frac{f^2}{d} + 233160 \quad \text{(Equation 1)}$$

As can be seen in the equation above, the system is configured such that the modulus is determined based on a thickness of the skin as well as on the resonant frequency. More specifically, the modulus is directly related to the square of the resonant frequency and inversely related to the thickness of skin. The resonant frequencies and moduli are tabulated in Table 1 for different tissues. As indicated for normal skin and scar tissue, the modulus values change as result of injury or disease so once a baseline modulus is determined for a particular tissue, changes in the modulus indicate some sort of injury or disease. Step 214 at FIG. 2 involves comparing the resonant frequency and modulus obtained with calibration Table 1 in order to determine if there are anomalies. The skin thickness d is determined from the OCT image. The OCT is utilized to measure the thickness of the skin d prior to the beginning of the vibrations (such as sound vibrations) since the skin is thin enough for the OCT to be able to penetrate its depth and create an image of it and, therefore, the thickness is measured from the image.

Figure 4:
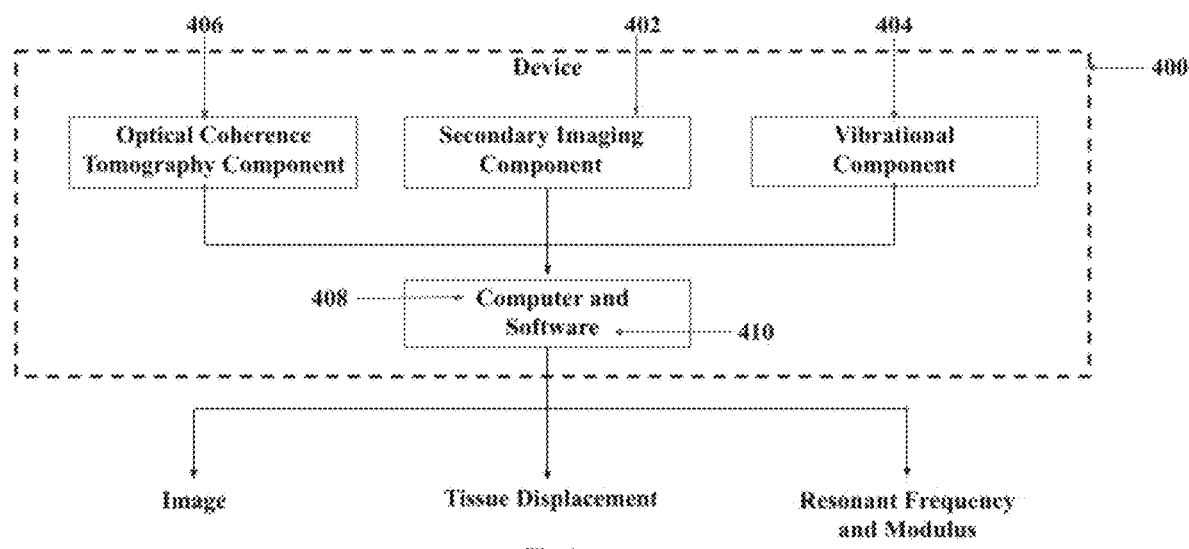
FIG. 4 shows a diagram specifying various components of a system according to an embodiment of the present invention.

FIG. 4 shows the components of OCT Device 400. These components can be part of a single device or can be individual components or some can be part of a single device and some individual components. If components are not part of the same device, they may need to be operably connected with one another. For example, the OCT component 406 is operably connected to the vibrational component 404. The secondary imaging component 402 of device 400 can be an ultrasound device which is used to determine the location of tissue 104 in FIG. 1b and the location of the marked skin 106. Secondary imaging component 402 does not necessarily have to be an ultrasound machine and may be any machine that can help identify the location of tissue 104 and the location of marked skin 106 can be utilized. Thus, FIG. 4 includes a diagram showing components of a device to image and measure the mechanical properties of subcutaneous tissues. The components include an optical coherence tomography device 406 capable of determining the tissue displacement that results from mechanical vibrations reflecting back to the outer surface of skin or a material when acted upon by the vibrational component, a secondary imaging component 402 capable of generating images of tissues below the skin and a computer 408 and software 410 capable of determining tissue displacements and calculating resonant frequencies and moduli. The secondary imaging component 402 can be part of the system as shown at FIG. 4 by being operably connected to the computer 410 such that it is operated by the computer, or it can be a separate component that is operated independently of the OCT component 406 and vibrational component 404.

At FIG. 4, the vibrational component 404 can be a wireless speaker though it does not necessarily have to be and any device that can vibrate skin and subcutaneous tissues such as marked skin 106 and tissue 104 (see FIG. 1b) can be utilized. The optical coherence tomography component 406 can be an OCT hand piece 406 and this is used to collect reflected infrared light from the surface of the marked skin 106 such as the skin corresponding to an Achilles tendon 102 (or other tissue to be studied). The optical coherence tomography component 406 can be a spectral-domain optical coherence tomography (SD-OCT) equipment 406, which is part of the system 400, or which can be separate from the system 400. Such equipment 406 may use a fiber optic coupled super luminescent diode light source with an 810 nm center wavelength and 100 nm bandwidth (full-width at half maximum) which is directed towards the marked skin 106.

Although the infrared light only penetrates about 0.5 to 1 mm into the skin, the audible sound (e.g., speaker sound) will penetrate deeper through the subcutaneous tissues. Deeper infrared light penetration can be achieved using light sources with wavelengths from 810 nm to 1320 nm. Preferably, the vibrational component 404 and the optical coherence tomography component 406 are operated simultaneously with the vibrational component 404 vibrating skin 106 and the OCT component 406 measuring displacement of the vibrating skin 106. The optical coherence tomography device 400 is used to measure the displacement of the tissue at different frequencies of the audible and inaudible spectrum. The optical coherence tomography device 400 controls both the audible sound which is applied to the tissue as well as the light which optical coherence tomography devices normally use to measure characteristics of tissues. The frequency of the audible sound is controlled through the OCT device 400. The OCT device 400 uses software 410 to generate sound in a wireless speaker (e.g., vibrational component 404) which creates displacement and is measured automatically in the OCT device 400. The OCT device 400 then determines displacement of the tissue at particular frequencies to then determine the maximum displacement and associated resonant frequency. Such frequency is the resonant frequency of the tissue. In other words, the OCT device 400 can be used in real time in conjunction with the audible sound (to vibrate the tissue) to determine the resonant frequency of the tissue due to the displacement of the tissue while vibrated by the audible sound.

For additional convenience, a device 400 can be used which has the OCT component 406 operably connected with the acoustic generator (such as the vibrational component 404) and can also include a universal mount designed as a hand piece so that the OCT component 406 can be used anywhere on a person's body. The user can then use ultrasound or other devices to determine the location of the tissue and the OCT device 400 to determine the resonant frequencies and, subsequently, the modulus. In the present application, the term "modulus" is a reference to E, an elastic modulus, or modulus of elasticity. In other words, a reference to "modulus" in the present application is a reference to a modulus which is characteristic of the elasticity of a material. Such a modulus could be what is known as the Young's Modulus. However, preferably, the "modulus" according to the present application is a modulus which is characteristic of the elasticity (or elastic component) of a material without being characteristic of the viscous component of a material. The Young's Modulus is a complex modulus with both viscous and elastic components and the objective of the present invention is to measure a modulus characteristic of the elastic component of a material, such as a Young's Modulus or, preferably, a modulus without a viscous component. Viscoelastic materials such as polymers and tissues have both viscous and elastic components. One of ordinary skill in the art would understand what is a modulus which is characteristic of the elasticity of a material such as the Young's Modulus or a modulus which differs from the Young's Modulus by not having a viscous component to it. The modulus of the present invention is, preferably, directly related to the square of the frequency (in Hertz) and is inversely related to the skin thickness (in meters). The OCT device 400 also uses software 410 to determine the thickness of the tissue.

Figure 5:
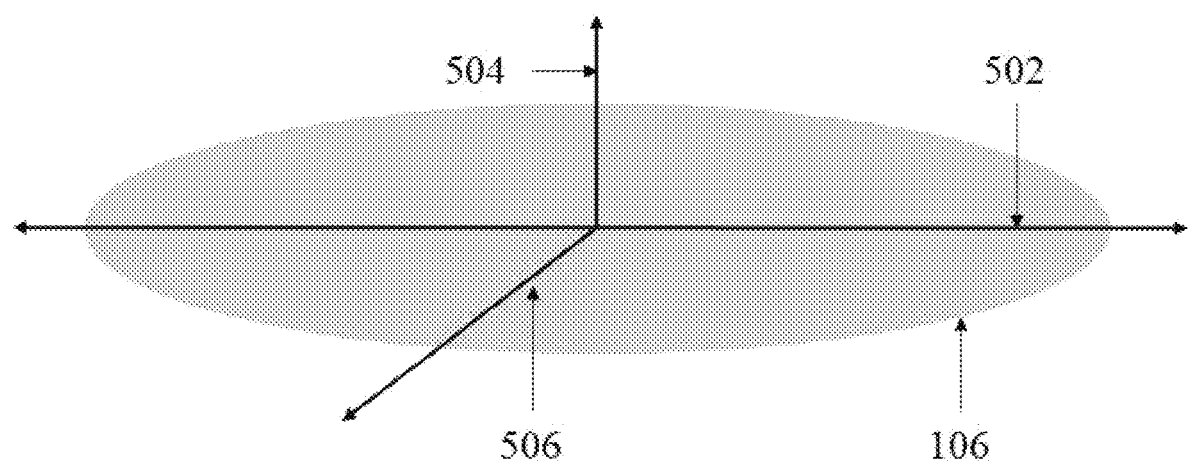
FIG. 5 shows a portion of skin to be analyzed in accordance with the present invention.

Preferably, the displacement of the skin 106 is transverse to the skin. In other words, the displacement of the skin is perpendicular to the surface of the skin. In an embodiment of this invention, the amplitudes of the vibrations extend at least 50% and preferably at least 75% transverse (i.e., perpendicular) to the skin as shown at FIG. 5. FIG. 5 shows skin 106 from FIG. 1 and a parallel line 502 which intersects at least two points on skin 106 and perpendicular line 504 is substantially perpendicular to the skin 106. For example, perpendicular line 504 may be substantially perpendicular to the plane formed by parallel line 502 and a line 506 which connects parallel line 502 and another point on the skin 106. The amplitude of skin vibrations may be W, and W can vary as the frequency of the vibrational component 404 varies (see FIG. 6). The component of W along line 504 is preferably at least 50% and more preferably at least 75% of the total value of W.

Once the skin is displaced in a transverse direction, the skin tissue will be deformed perpendicular to the surface of the skin and when stimulation is removed the tissue will recover from such deformation in a direction perpendicular to the surface of the skin.

Another advantage of the OCT component 406 is that it preferably utilizes coherent light. The signal reflected back to be analyzed by the OCT device 400 should preferably be coherent relative to the signal emitted by the OCT device 400 in order to figure out the in phase and out of phase of the signal. Preferably, the OCT signal reflected back should be at least 50%, and preferably at least 75%, coherent relative to the signal which is emitted by the OCT device. It is noted that the OCT device 400 can be calibrated, unlike other possible techniques for analyzing tissue.

The OCT component 406 basically will analyze the signals at the skin 106. In the present application, another way to refer to the skin 106 or other surface where the OCT device detects signals is the "outer surface" since it is the outermost portion of the mass which is being evaluated and this does not have to be skin since the present invention can be used in non-skin applications.

As stated above, the vibrational component 404 can generate an electric field or a magnetic field instead of sound vibrations. This is because electric current can displace skin and so can a magnetic field. The OCT component 406 can measure vibrations generated by electric fields and magnetic fields in the skin to determine the resonant frequency instead of using sound.

Figure 6:
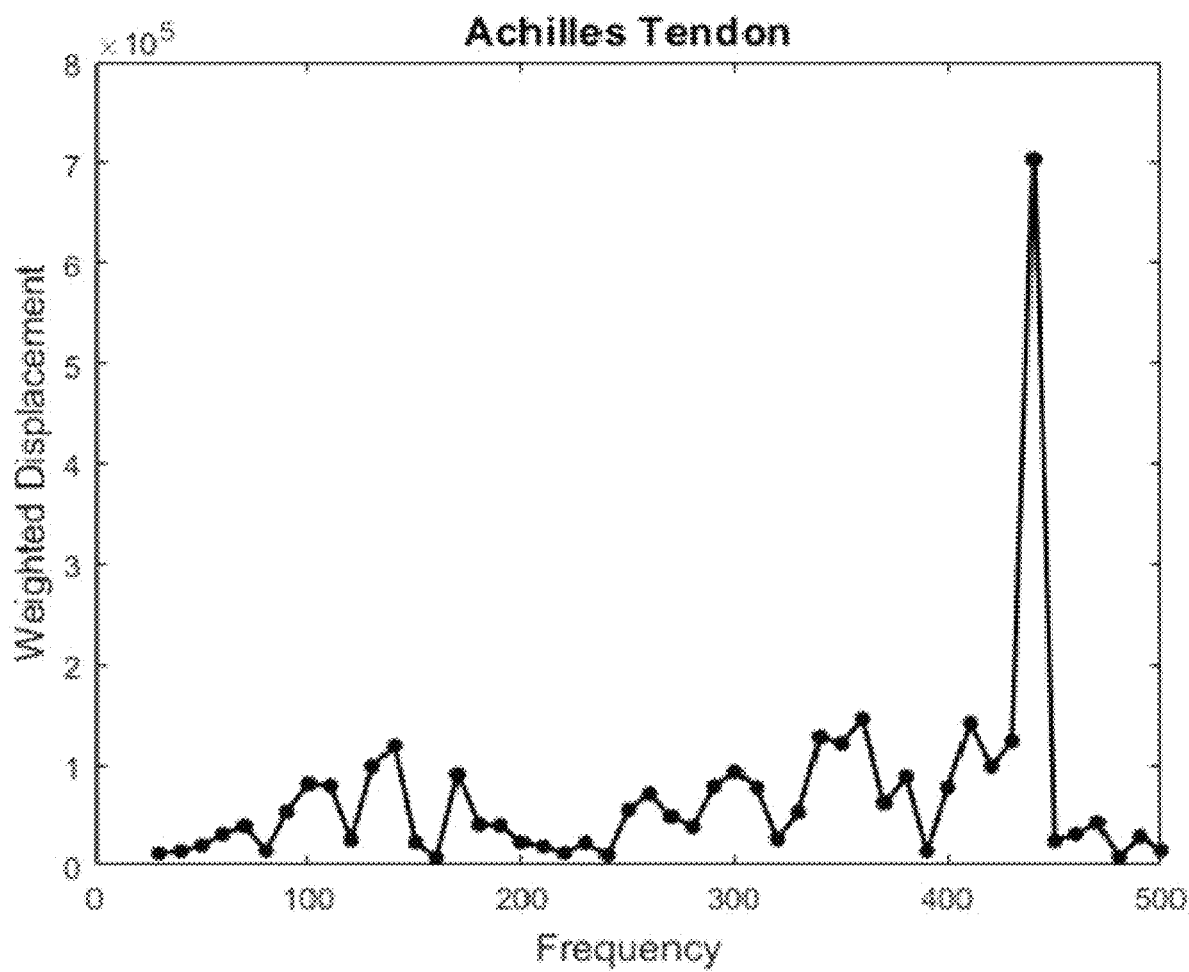
FIG. 6 shows a diagram of frequency versus displacement for tissue in an Achilles tendon.

Resonant frequency is the lowest frequency at which one can obtain maximum displacement of the skin in a direction along line 504 in FIG. 5. Maximum tissue and material motion or displacement can be obtained at the fundamental frequency of resonance, in this case skin movement along line 504 in FIG. 5. Thus, if the vibrational component 404 generates sound waves, and these sound waves vibrate the skin 106, these vibrations will propagate into internal organs and are projected back on to the skin surface. The bulk resonant frequency is measured at the outer surface of skin 106 and reflects the characteristic components of the structures below the skin 106. In other words, the skin 106 is getting vibrations from tissues 104 below and therefore reflects the mechanical properties of the tissues 104 below. In the case of the OCT component 406, a spectral image of the skin is analyzed to obtain the resonant frequency of each macromolecular component of tissues below the surface, with different tissue components potentially having different resonant frequencies, as shown in Table 1. Peaks from a spectrum of displacement vs frequency are tabulated in Table 1. Skin has peaks of 50 Hz with respect to dermal cells, 100 Hz with respect to dermal collagen, 150 Hz with respect to blood vessels, and 210 Hz to 230 Hz with respect to scar tissue. Frequency spectra are generated which are characteristic of the resonant frequency for each component of tissue under measurement. For example, one spectral image can generate resonant frequency peaks (such as shown in FIG. 6.) which result in the delineation of multiple component peaks in one spectral image characterizing dermal cells and collagen, blood vessels and scar tissue. This makes the technique a tissue or polymer spectral analyzer. The OCT device 400 determines the resonant frequency for each component at the highest perpendicular displacement to the skin 106 (e.g., along line 504).

The transverse displacement measured at the skin surface is the result of the transverse vibrations imparted to the bulk tissue, though it is possible to measure displacement which is not perpendicular to the skin 106. Thus, if the vibrational component 404 generates sound waves, and these sound waves vibrate the skin 106, these vibrations will propagate into internal organs and are then reflected back to the skin, and the resonant frequency is measured at the skin 106 (e.g., "outer surface") which reflects the changes which are happening below the skin 106. In other words, the skin 106 is getting vibrations from tissues 104 below and therefore reflects the mechanical properties of the tissues 104 below. In the case of the OCT component 406, light reflected from the skin is analyzed to get the resonant frequency of each macromolecular component of tissues since different tissue components may have different resonant frequencies, as shown in Table 1. Thus, peaks show up in a plot of displacement vs frequency at the frequencies noted in Table 1. Skin has peaks of 50 Hz for cells, 100 for dermal collagen, 150 for blood vessels, and 210 to 230 for scar tissue. In other words, the frequency generator will generate vibrations at different frequencies and one spectra of vibrations at different frequencies can generate a resonant frequency for each component of tissue being measured so one "pass" of frequencies (such as shown at FIG. 6) can result in the determination of resonant frequencies for multiple components such as cells, dermal collagen, blood vessels, and scar tissue, which makes this procedure very efficient. The OCT device 400 helps determine displacement at each frequency, and the highest displacement perpendicular to the skin 106 (e.g., along line 504) at the lowest frequency is the resonant frequency for each component.

Preferably, the displacement measured is transverse to the skin since the vibrations are preferably transverse to the skin, though it is possible to measure displacement which is not perpendicular to the skin 106. The results of the measurement of displacement versus frequency is shown at FIG. 6 in the case of an Achilles tendon. FIG. 6 shows a plot of weighted displacement versus frequency for human Achilles tendon as described in FIG. 1. It is noted that at FIG. 6, the resonant frequency of skin is about 100 Hz and that of Achilles tendon is 440 Hz. The other minor peaks are from other structures that are near the Achilles tendon.

The system of the present invention can include an optical coherence tomography device configured to receive frequency data (e.g., spectral image data) and configured to measure displacement of skin tissue to generate displacement data (e.g. a spectral map). The system further includes one or more processors and one or more data storage devices with instructions stored therein. Those instructions (which are software), can be executed by the one or more of the processors to cause the one or more of the processors to perform operations including processing of the frequency data (e.g., from a speaker or other device) and the displacement data of the OCT device or other device, to determine a modulus as explained below.

An aspect of the invention involves calculating the modulus E. This is shown as step 212 at FIG. 2. The modulus, E, is computed from the frequencies, f, at which the maximum displacements of the tissues are observed in the skin (e.g., the resonance frequencies). A stronger signal is achieved when the displacement is transverse to the skin surface 106. Preferably, the displacement measured is transverse to the skin 106. When the skin 106 is vibrated, the resonant frequency of both the Achilles tendon, including tissue 104, and skin 106 will be measured. For example, dermal collagen resonates at about 100 Hz and Achilles tendon resonates at about 440 Hz which is reflected back to the skin and imaged at the skin surface. This is why the frequency is varied as a function of time in order to vibrate different structures in the tissue below. Thus, skin will resonate at 100 Hz (collagen) and 440 Hz (tendon) and at every frequency that subcutaneous tissues resonate at as shown in Table 1. This is why it's important to properly place the OCT handpiece in order to measure the appropriate tissue below the surface. The peak heights will reflect the location above the tissue so when the OCT is above a tendon, there will be a peak for a tendon, as well as for collagen since both are present. In this example, the tendon resonance peak is bigger than the one for skin. This is an indication of the amount of component tissue present in the underlying tissue bulk. Thus, the displacement of tissue is higher at 440 Hz than 100 Hz. The modulus E is measured (FIG. 6) using the Equation 1 where d is the skin thickness in meters and E is in Pascals and f is in Hertz, $$E = 0.0654 * \frac{f^2}{d} + 233160 \qquad \text{(Equation 1)}$$

The letter "f" is the resonant frequency of the macromolecular component being measured, and as included in Table 1. For example, at FIG. 6 there is a peak at a frequency of around 440 Hz which by definition in Table 1 is the Achilles tendon which has an elastic modulus of 34 MPa.

The resonant frequencies and moduli are tabulated in Table 1 below for different tissues. As indicated for normal skin and scar tissue, the modulus values change as a result of injury or disease. The skin thickness d is determined from the OCT image from the OCT component 406. The OCT component 406 is utilized to measure the thickness of the skin d prior to the beginning of the vibrations (such as sound vibrations) since the skin is shallow enough for the OCT component 406 to penetrate its thickness and make a measurement from the image.

FIG. 7 shows a schematic diagram showing optical coherence tomography and vibrational components shown in FIG. 4 used in determining the resonant frequency of subcutaneous tissues. Coherent 810 nm infrared beam of light is projected onto the skin location surface (i.e., "outer surface") and some of it penetrates the surface while the rest is reflected back from the outer surface. The reflected light from the surface is combined with a reference beam of the same wavelength as the incident beam to produce a spectral image of the phase differences between the reflected beam and the reference beam at every point along the scanned image under measurement. A sinusoidal sound wave is applied to the outer surface of the skin that penetrates the underlying tissues. The displacement of the skin outer surface by the acoustically vibrated tissue below creates an interferometric pattern on the skin surface from the underlying tissue structures. The interferometric pattern is analyzed by the OCT spectral analyzer to create a spectral (frequency) image of the underlying tissue structures in the frequency domain. The spectral image contains the characteristic resonant frequencies of the underlying tissue structures that are then converted into the characteristic frequency spectrum of the tissue structure moduli. The modulus is calculated using equation (1), as explained above. VOCT 702 in the diagram refers to an OCT device capable of measuring vibrations of samples that occur in the 30 to 20,000 Hz range. The reference arm contains the part of the light source that is not directed at the sample. VOCT is an OCT device that can obtain a spectral image from an acoustically vibrating surface and is customized to include the software of the present invention. The VOCT is operably connected with the device that vibrates the materials under investigation or test so as to determine resonant frequencies of those materials. The reference arm contains fiber optic (or other transmission device) to deliver and receive light in the case of an OCT. The customized VOCT device may have proprietary software on the hard drive that is used to tabulate the weighted displacement as a function of frequency required to calculate the modulus.

Example 1

Tests were conducted on volunteers with ages ranging from 24 to 70 years old after informed consent was obtained. All studies were conducted at 75° F. and 40% to 50% relative humidity. A frequency generating app was downloaded onto the I5 processor within the OCT device 400. This app was capable of driving the speaker (which was also part of the system) between 30 and 20,000 Hz. The speaker was placed in several locations over the tissue being studied but was not in contact with the skin. During in vivo measurements, no sensation of the light or sound is felt by the subject. The sample displacement was then measured as a function of frequency after the speaker was activated by the computer within the OCT. The raw image of the skin was obtained instantaneously from the OCT camera and analyzed using the software on the computer hard drive.

The weighted displacement versus frequency curve becomes a mechanical spectrum generated by the components of the tissues that vibrate (see, e.g., FIG. 6). Weighted displacement is normalized by dividing by the displacement of the speaker when the data is collected in the absence of the tissue.

Once the modulus is determined, it can be used to determine differences between normal skin and cancerous lesions or fibrotic disorders. Normal tissue components have a particular modulus (see Table 1) so if the modulus which is determined is different, this is an indication that the tissue is not normal. The modulus can even be used to determine the extent of fibrotic disorder in skin. In other words, the determination of the modulus allows the determination of whether the skin or other tissue is different from normal skin and is therefore an inexpensive way to determine abnormalities without cutting or dangerous radiation, or discomfort in a patient, and can be done in-situ in real time without having to wait days or more for a laboratory analysis. Once the information is gathered with respect to a particular tissue, this can be compared with predetermined data for that particular tissue. For example, Table 1 below shows the resonance frequency and modulus of different components of tissues.

The OCT device 400 is also capable of calculating the viscoelasticity of material. By pulsing a sound sinusoidal wave against the material, and using the OCT device 400 to measure the sound waves, the viscoelasticity of the material can be determined from the width of the weighted displacement versus frequency peaks at the half height of the peak after the sound vibrations have been terminated. The sound causes movement of the material and this is detected by the OCT device 400 and, thus, the sound affects the light of the OCT device 400 and this is used to determine the viscoelasticity. Such viscoelasticity can be used to determine properties of synthetic polymers such as rubbers, as well as metals, ceramics and composite materials.

TABLE 1

Data showing the resonant frequency and moduli for various internal and external tissue components and polymeric materials obtained using the device described and diagrammed in FIG. 7.

| Tissue | Resonant Frequency (Hz) {SD} | Modulus E (MPa) {SD} |
|---|---|---|
| Bone | | |
| Lamellar Bone | 990 | 173 {20} |
| Subchondral Bone | 590 | 65.34 |
| Ear and Alar cartilage | 280 | 12.05 |
| Fat, Epidermal Cells | 40-70 | 1.11 {0.25} |
| Fibrotic Tissue | 220 | 7 |
| Ligament | | |
| Anterior Cruciate Ligament (ACL) | 520 | 52.3 |
| Medial Collateral Ligament (MCL) | 280 | 12.4 |
| Meniscus | 430 | 31.4 {3.37} |
| Muscles | | |
| Bicep Muscle | 378.33 {16.02} | 29.6 {2.62} |
| Quadriceps Muscle | 365 {21.21} | 20.5 {2.32} |
| Nerve | | |
| Facial Nerve | 260 | 14.65 |
| Radial Nerve | 280 | 14.49 |
| Ulnar Nerve | 260 | 18.45 |
| Normal Skin | 110 | 2.15 {0.29} |
| Ocular | | |
| Cornea | 130 | 2.5 |
| Lens | 170 | 2.4 |
| Sclera | 150 | 2.3 |
| Tendon | | |
| Achilles Tendon | 440 | 34.0 {5.98} |
| Finger Flexor Tendon | 350 | 23.2 |
| Flexor Digitorum Profundus Tendon | 360 | 16.03 |
| Patellar Tendon | 430 {5.77} | 33.8 {4.62} |
| Vascular | | |

TABLE 1-continued

Data showing the resonant frequency and moduli for various internal and external tissue components and polymeric materials obtained using the device described and diagrammed in FIG. 7.

| | | |
|---|---|---|
| Carotid Artery | 160 | 5.78 |
| Radial Artery | 155 {11.98} | 3.66 {0.65} |
| Vein | 160 | 4.35 |

| Sample | Resonant Frequency (Hz) {SD} | Modulus E (MPa) {SD} |
|---|---|---|
| ABS Plastic | 2800 {10.0} | 2120 {0.02} |
| Silicone Rubber | 80 {10.0} | 1.68 {0.23} |
| New Viton Gasket | 180 {5.0} | 11.45 {0.64} |
| Old Viton Gasket | 140 {5.0} | 5.99 {0.43} |

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic.

Further, repeated use of the phrase "in one embodiment," or "in an illustrative embodiment," do not necessarily refer to the same embodiment, although they may. The various embodiments described herein may be combined and/or features of the embodiments may be combined to form new embodiments.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors and/or databases.

While various embodiments of the invention have been described above, it should be understood that they have been presented by way of example only, and not limitation. Thus, the breadth and scope of the invention should not be limited by any of the above-described illustrative embodiments. The embodiments of the invention that have been described above may contain features that may be removed or combined between the described embodiments to derive additional embodiments. Any range disclosed herein is intended to disclose and discloses any range within such disclosed range.

Headings and subheadings, if any, are used for convenience only and do not limit the invention.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. Furthermore, to the extent that the term "include," "have," or the like is used in the description or the claims, such term is intended to be inclusive in a manner similar to the term "comprise" as "comprise" is interpreted when employed as a transitional word in a claim.

What is claimed:

1. A system comprising a first device configured to utilize electromagnetic waves to determine a resonant frequency of induced vibrations of at least one component of bulk material or subcutaneous tissue, and a second device operably connected to the first device and configured to generate the induced vibrations, wherein the first device and the second device are operably connected to each other and are part of a same piece of equipment or are separate pieces of equipment, wherein the first device is configured to determine the resonant frequency of the at least one component of the bulk material or the subcutaneous tissue through reflected vibrations reflected from the bulk material or subcutaneous tissue to an outer surface of the bulk material or subcutaneous tissue wherein one or more processors forming part of the system or operably connected to the system are configured to determine a modulus of the at least one component of the bulk material or the subcutaneous tissue based on a thickness of skin as well as on the resonant frequency.

2. The system according to claim 1, wherein the first device is configured to receive frequency data from the second device and to process such frequency data to determine the resonant frequency of the induced vibrations of the at least one component of bulk material or subcutaneous tissue.

3. The system according to claim 2, wherein the first device comprises the one or more processors and one or more data storage devices, and wherein a first of the data storage devices stores the frequency data and wherein the first or a second of the data storage devices comprises instructions stored therein, which when executed by the one or more processors, cause the one or more processors to perform operations including processing of the frequency data.

4. The system according to claim 1, wherein the first device is an optical coherence tomography device and wherein the second device is configured to generate sound vibrations or other mechanical vibrations to induce the induced vibrations.

5. The system according to claim 1, wherein the second device comprises a sound generator.

6. The system according to claim 1, wherein the induced vibrations have frequencies of between 30 and 20,000 Hertz, and wherein the induced vibrations comprise sinusoidal audible sound vibrations with variable frequency as a function of time.

7. The system according to claim 1, wherein the second device comprises a piezoelectric device or a speaker.

8. The system according to claim 1, wherein the first device is configured to determine the resonant frequency by measuring displacement of the bulk material or subcutaneous tissue as a function of the frequency or time of the induced vibrations.

9. The system according to claim 1, wherein the system is configured to conduct at least one selected from the group consisting of: determining a degree of injury to a subcutaneous tissue based on changes in tissue stiffness; evaluating efficacy of treatment to improve wound healing or ameliorate disease of skin; evaluating efficacy of treatments to alter the effects of aging of skin; evaluating deposition of fat and fibrosis of the liver; evaluating deposition of lipids and minerals or the presence of aneurysms that lead to stenosis or dissection of arteries, lymphatics or veins; evaluating tissue dysplasia and fibrosis of reproductive tissues in women and testes in males; evaluating urinary and digestive tracts in males and females; evaluating lung fibrosis, esophageal changes and mucin deposition in the airways; evaluating heart septal defects, valvular stenosis and ventricular hypertrophy; evaluating pulmonary artery insufficiency; evaluating muscular atrophy, fibrosis and tissue damage; evaluating nerve crush injuries and results of nerve entubulation repairs; evaluating repair of tendons and ligaments using autografts and allografts; evaluating normal and diseased ocular tissues including lens, cornea, sclera, retina, lamina cribosa and optic nerve; evaluating stress fractures in bone and cranium; evaluating tears and evulsions of tendons and ligaments; evaluating efficacy and degradation rates of implanted medical devices evaluating the biological compatibility, irritation, reactivity and the lifespan of implants in animals; evaluating cell density and protein deposition of cell and tissue components in tissue cultures; evaluating cartilage in joints and ear; evaluating repair of tendons, vessels, joint components and ligaments in the hands, joints and feet; evaluating bacterial and viral contamination, infection and healing of wounds and skin ulcers; evaluating fat deposition and fibrosis in the liver; evaluating blood smears and tissue aspirates; evaluating kidney function and fibrosis; evaluating bone, perichondrium and periosteum as source of growth factors, stem cells or tissue transplants; evaluating breast tissue or breast biopsies for the presence of fibrosis, cancerous tumors and calcifications; evaluating prostate, thyroid and lymph nodes; and evaluating skin lesion, cancers, inflammation and other proliferative diseases.

10. The system according to claim 1, wherein the modulus is directly related to the resonant frequency and inversely related to the thickness of skin.

11. The system according to claim 1, wherein the modulus is determined in accordance with the following equation in which E is the modulus in Pascals, d is the thickness of skin in meters, and f is the resonant frequency of the induced vibrations:

$$E = 0.0654 * \frac{f^2}{d} + 233160.$$

12. The system according to claim 1, wherein the at least one component of bulk material or subcutaneous tissue comprises a plurality of components of bulk material or subcutaneous tissue and wherein the resonant frequency of each of the plurality of components of bulk material or subcutaneous tissue is determined from a single spectrum of the induced frequencies.

13. The system according to claim 1, wherein the second device comprises a speaker.

14. The system according to claim 1, wherein the first device is an optical coherence tomography device and the second device is a speaker configured to produce audible sound waves.

15. A system comprising a first device configured to utilize electromagnetic waves to determine a resonant frequency of induced vibrations of at least one component of bulk material or subcutaneous tissue, and a second device operably connected to the first device and configured to generate the induced vibrations, wherein the first device and the second device are operably connected to each other and are part of a same piece of equipment or are separate pieces of equipment, wherein the first device is configured to determine the resonant frequency of the at least one component of the bulk material or the subcutaneous tissue through reflected vibrations reflected from the bulk material or subcutaneous tissue to an outer surface of the bulk material or subcutaneous tissue, and wherein the second device is configured such that the induced vibrations extend at least 50% transversely to the outer surface.

16. A system comprising an optical coherence tomography device and a sound generator to vibrate tissue, the optical coherence tomography device being configured to receive frequency data and configured to measure displacement of skin tissue to generate displacement data, the system further comprising one or more processors and one or more data storage devices with instructions stored therein, which when executed by the one or more processors, cause the one or more processors to perform operations including processing of the frequency data and the displacement data to determine a resonant frequency and a modulus of tissue, and wherein the modulus of the tissue is determined based on a thickness of skin as well as on the resonant frequency.

17. A method of determining (A) a modulus of at least one component of a bulk material or subcutaneous tissue through reflected vibrations reflected from the bulk material or subcutaneous tissue to an outer surface of the bulk material or subcutaneous tissue and (B) a resonant frequency of vibrations of the bulk material or subcutaneous tissue, comprising vibrating the outer surface of the bulk material or subcutaneous tissue with induced vibrations having varying frequencies as a function of time to vibrate the bulk material or subcutaneous tissue and determining displacement of the outer surface with electromagnetic waves, and utilizing the frequencies of the induced vibrations and the displacement of the outer surface to determine the modulus and the resonant frequency, wherein determination of the modulus is based on skin thickness and the resonant frequency.

* * * * *